(12) United States Patent
Dalton

(10) Patent No.: US 9,162,054 B2
(45) Date of Patent: Oct. 20, 2015

(54) IMPLANTABLE COMPONENT INTERFACE

(75) Inventor: James W. Dalton, Beecroft (AU)

(73) Assignee: COCHLEAR LIMITED, MacQuarie University, NSW (AU)

( * ) Notice: Subject to any disclaimer, the term of this patent is extended or adjusted under 35 U.S.C. 154(b) by 1613 days.

(21) Appl. No.: 12/524,148

(22) PCT Filed: Jan. 22, 2008

(86) PCT No.: PCT/AU2008/000050
§ 371 (c)(1),
(2), (4) Date: Jul. 20, 2011

(87) PCT Pub. No.: WO2008/089505
PCT Pub. Date: Jul. 31, 2008

(65) Prior Publication Data
US 2013/0184804 A1    Jul. 18, 2013

(30) Foreign Application Priority Data

Jan. 22, 2007   (AU) ................ 2007900299

(51) Int. Cl.
| | | |
|---|---|---|
| *A61N 1/00* | (2006.01) | |
| *A61N 1/05* | (2006.01) | |
| *A61N 1/375* | (2006.01) | |
| *A61F 11/00* | (2006.01) | |
| *A61N 1/36* | (2006.01) | |

(52) U.S. Cl.
CPC .............. *A61N 1/0541* (2013.01); *A61N 1/375* (2013.01); *A61F 11/004* (2013.01); *A61F 2220/0008* (2013.01); *A61N 1/36032* (2013.01)

(58) Field of Classification Search
CPC ......... A61N 1/02; A61N 1/372; A61N 1/375; A61N 1/44; A61F 2/00; A61F 2/02; A61F 2/04; A61F 2/18; A61F 2/82; A61F 2/852; A61B 1/00; A61B 1/012; A61B 1/24
See application file for complete search history.

(56) References Cited

U.S. PATENT DOCUMENTS

| | | | | |
|---|---|---|---|---|
| 4,495,917 | A |    | 1/1985 | Byers |
| 5,578,084 | A | * | 11/1996 | Kuzma et al. ................... 623/10 |
| 6,662,035 | B2 | * | 12/2003 | Sochor .......................... 600/378 |
| 2003/0074076 | A1 |  | 4/2003 | Ferree et al. |
| 2005/0113932 | A1 |  | 5/2005 | Kovacevic |
| 2005/0245996 | A1 |  | 11/2005 | Phillips et al. |
| 2005/0267543 | A1 | * | 12/2005 | Heruth et al. ................... 607/36 |

FOREIGN PATENT DOCUMENTS

WO    01/39830    6/2001

OTHER PUBLICATIONS

PCT International Preliminary Report on Patentability for PCT/AU2008/000050 dated May 1, 2009.
PCT Written Opinion of the International Searching Authority for PCT/AU2008/000050 dated Feb. 27, 2008.
PCT International Search Report for PCT/AU2008/000050 dated Mar. 25, 2008.

* cited by examiner

*Primary Examiner* — Christopher D Koharski
*Assistant Examiner* — Elizabeth K So

(57) ABSTRACT

An implantable medical device, comprising a first implantable component having a first interface surface and a second implantable component. The second implantable component has a second interface surface comprising one or more integrated protrusions extending therefrom configured to mate with the first interface surface and to provide a desired spacing between the first and second implantable components.

27 Claims, 7 Drawing Sheets

IMPLANTABLE COMPONENT INTERFACE

CROSS REFERENCE TO RELATED APPLICATIONS

This application is a National Stage of PCT/AU2008/000050, filed Jan. 22, 2008, which claims priority from Australian Provisional Patent Application No. 2007900299 entitled "COCHLEAR IMPLANT UPGRADE METHOD AND APPARATUS," filed Jan. 22, 2007. The contents of these applications are hereby incorporated by reference herein.

FIELD OF THE INVENTION

The present invention relates generally to components of an implantable medical devices and, more particularly, to an implantable component interface.

RELATED ART

Medical devices having one or more implantable components, generally referred to as implantable medical devices, have provided a wide range of therapeutic benefits to patients over recent decades. Implantable hearing prostheses that treat the hearing loss of a prosthesis recipient are one particular type of implantable medical devices that are widely used today.

Hearing loss, which may be due to many different causes, is generally of two types, conductive and sensorineural. In some cases, a person suffers from hearing loss of both types. Conductive hearing loss occurs when the normal mechanical pathways for sound to reach the cochlea, and thus the sensory hair cells therein, are impeded, for example, by damage to the ossicles. Individuals who suffer from conductive hearing loss typically have some form of residual hearing because the hair cells in the cochlea are undamaged. As a result, individuals suffering from conductive hearing loss typically receive an implantable hearing prosthesis that generates mechanical motion of the cochlea fluid. Some such hearing prosthesis, such as acoustic hearing aids, middle ear implants, etc., include one or more components implanted in the recipient, and are referred to herein as implantable hearing prosthesis.

In many people who are profoundly deaf, however, the reason for their deafness is sensorineural hearing loss. Sensorineural hearing loss occurs when there is damage to the inner ear, or to the nerve pathways from the inner ear to the brain. As such, those suffering from some forms of sensorineural hearing loss are thus unable to derive suitable benefit from hearing prostheses that generate mechanical motion of the cochlea fluid. As a result, implantable hearing prostheses that deliver electrical stimulation to nerve cells of the recipient's auditory system have been developed to provide the sensations of hearing to persons whom do not derive adequate benefit from conventional hearing aids. Such electrically-stimulating hearing prostheses deliver electrical stimulation to nerve cells of the recipient's auditory system thereby providing the recipient with a hearing percept.

As used herein, the recipient's auditory system includes all sensory system components used to perceive a sound signal, such as hearing sensation receptors, neural pathways, including the auditory nerve and spiral ganglion, and parts of the brain used to sense sounds. Electrically-stimulating hearing prostheses include, for example, auditory brain stimulators and cochlear prostheses (commonly referred to as cochlear prosthetic devices, cochlear implants, cochlear devices, and the like; simply "cochlear implants" herein.)

Oftentimes sensorineural hearing loss is due to the absence or destruction of the cochlear hair cells which transduce acoustic signals into nerve impulses. It is for this purpose that cochlear implants have been developed. Cochlear implants provide a recipient with a hearing percept by delivering electrical stimulation signals directly to the auditory nerve cells, thereby bypassing absent or defective hair cells that normally transduce acoustic vibrations into neural activity. Such devices generally use an electrode array implanted in the cochlea so that the electrodes may differentially activate auditory neurons that normally encode differential pitches of sound.

Auditory brain stimulators are used to treat a smaller number of recipients with bilateral degeneration of the auditory nerve. For such recipients, the auditory brain stimulator provides stimulation of the cochlear nucleus in the brainstem.

Totally or fully implantable forms of the above and other implantable hearing prostheses have been developed to treat a recipient's conductive, sensorineural and/or combination hearing loss. As used herein, a totally implantable hearing prosthesis refers to an implantable prosthesis that is capable of operating, at least for a period of time, without the need for any external device.

SUMMARY

In one aspect of the present invention a cochlear implant system is provided. The cochlear implant system comprises a first implantable component having a first interface surface; and a second implantable component having a second interface surface comprising one or more integrated protrusions extending there from configured to mate with the first interface surface and to provide a desired spacing between the first and second implantable components.

In another aspect of the present invention an implantable medical device is provided. The implantable medical device comprises a first implantable component having a first interface surface; and a second implantable component having a second interface surface comprising one or more integrated protrusions extending there from configured to mate with the first interface surface and to provide a desired spacing between the first and second implantable components.

BRIEF DESCRIPTION OF THE DRAWINGS

Exemplary embodiments of the present invention are discussed below with reference to the accompanying drawings, in which.

DETAILED DESCRIPTION

Aspects of the present invention are generally directed to an implantable medical device comprise two or more implantable components. More particularly, the implantable medical device comprises a first implantable component having a first interface surface; and a second implantable component having a second interface surface. The second interface surface comprises one or more integrated protrusions extending there from configured to mate with the first interface surface, and to provide a desired spacing between the first and second interface surfaces.

Embodiments of the present invention are primarily described herein with reference to one type of implantable hearing prosthesis, namely a cochlear prosthesis (commonly referred to as prosthetic device, cochlear implant, cochlear device, and the like; sometimes referred to as "cochlear implant systems" herein). It would be appreciated that embodiments of the present invention may be implemented in any implantable hearing prosthesis or other implantable medical device now known or later developed.

Figure 1:
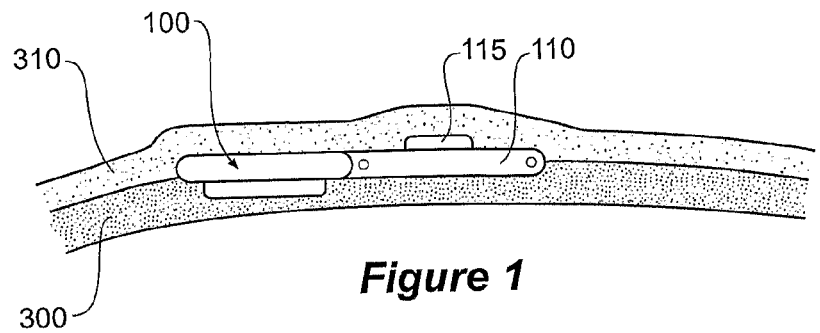
FIG. 1 is a side sectional view of an ICS unit according to the prior art.

Certain cochlear implant system includes an external sound pickup device, such as a microphone, coupled to a powered external speech processor (SP) unit. The SP converts the detected acoustic information to electrical information which is then transmitted to an implanted cochlear stimulator (ICS) which functions to drive an electrode array that is inserted within the cochlea. FIG. 1 illustrates one exemplary ICS 100.

ICS 100 is implanted subdermally or subcutaneously into a section of a recipient's skull 300 generally behind the recipient's ear and usually underneath the periosteum 310 located under the skin of the recipient. Information is transferred between an external SP unit and ICS 100 by virtue of respective external and internal electromagnetic communication coils that are inductively coupled.

Figure 4:
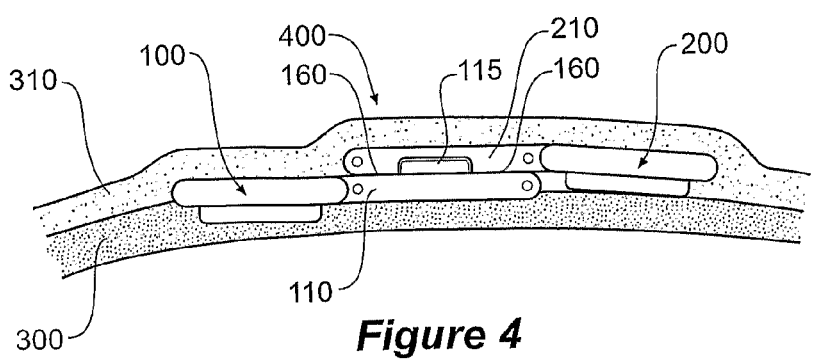
FIG. 4 is a side sectional view of the ICS and ISP units after the cochlear implant upgrade depicting the overlaying coils.

FIG. 4 illustrates an alternative cochlear implant system 400. In this arrangement, an implanted speech processor (ISP) 200 is communicatively coupled to ICS 100 by virtue of respective electromagnetic coil portions 210, 110. Typically the ISP 200 also includes a battery or charging device (not shown) which may be inductively charged by an external charging unit. Combined with a complete-in-canal (CIC) or otherwise implanted microphone (not shown), the entire cochlear implant system 400 is fully implantable. Because ISP 200 and ICS 100 are separate modules, it is possible to independently upgrade either component. This simplifies surgical procedures because there is no need to replace a bulky modular unit that includes the functionality of both an ICS and an ISP.

Another upgradeable architecture for a cochlear implant system involves an ICS 100 having a communication coil 110 which is driven externally by an external SP as discussed earlier. This system can then be upgraded to a fully implantable cochlear implant system by implanting an ISP 200 which communicates with the ICS 100 by virtue of a corresponding electromagnetic communication coil portion 210 which overlays the ICS electromagnetic communication coil portion 110 after implantation resulting in an arrangement such as that depicted in FIG. 4. However, this upgradeable architecture has a number of disadvantages, the most significant being that soon after the original ICS unit is implanted in the body, the device becomes encapsulated in a fibrous tissue layer 310 making it difficult to then implant an ISP in a subsequent surgical procedure which necessarily includes an electromagnetic communication coil 210 that overlays the corresponding ICS communication coil 110 such as illustrated in FIG. 4.

Figure 2:
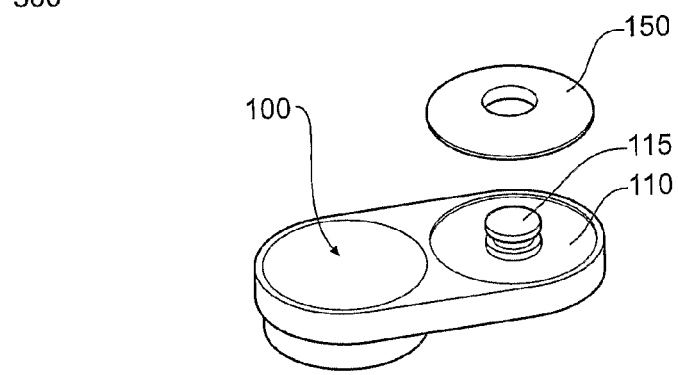
FIG. 2 is a top perspective exploded view depicting a removable silicone disc employed in conjunction with the ICS unit illustrated in FIG. 1 according to the prior art.
Figure 3:
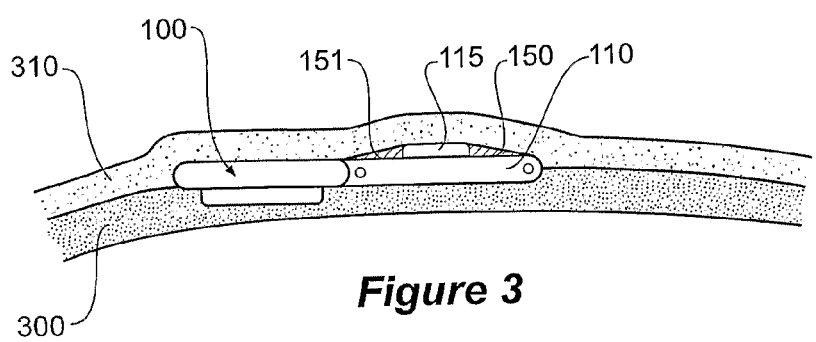
FIG. 3 is a side sectional view of the silicone disc illustrated in FIG. 2 forming part of the ICS unit.

Referring to FIGS. 2 and 3, one attempt to address this problem is to fit the initial implant 100 with an implantable component in the form of a removable disc of silicone 150, which locates around the magnet 115 which is located at the centre of the coil portion 110 in the ICS 100. This magnet 115 functions to hold an external headpiece and its corresponding coil in alignment with the electromagnetic communication coil 110 of the ICS unit 100. Thus, there is an interface 151 between disc 150 and ICS 100. Disc 150 is removed as part of the surgical procedure to install ISP 200.

Figure 5:
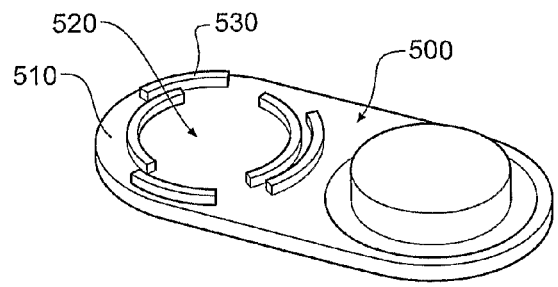
FIG. 5 is a bottom perspective view of an interface surface of an ISP unit according to a first illustrative embodiment of the present invention.

A cochlear implant component 500 in accordance with a first embodiment of the present invention is illustrated in FIG. 5. As shown, cochlear implant component 500, referred to as ISP 500, has an interface surface 520 comprising integrated spacing means or members 530 extending there from. Spacing means 530 comprise extensions arms that integrated into, and project from, surface 520. In the specific embodiments of FIG. 5, spacing means 530 comprise concentric protrusions 530 in the coil portion 510. In certain embodiments, protrusions have a semi-circular cross-sectional shape, while in other embodiments the protrusions have a substantially circular cross-sectional shape.

During use, interface surface 520 is positioned adjacent a corresponding interface surface of an ICS so that the tips of protrusions 530 mate with the corresponding interface. Thus, protrusions 530 space ISP 500 and an ICS a predetermined distance apart, thereby allowing fluid to freely flow between the two surfaces.

There is a potential for bacteria to develop when two implanted components are positioned in contact with one another. The implant conditions necessary to create and harbor bacteria are dependent on a number of factors including the vascularity of the tissue in the vicinity, the initial cleanliness of the mating parts, and the area in contact. By spacing the ICS and ISP interface surfaces from one another, the flow of fluid there between may flush bacteria from the mating area. Additionally, because only protrusions 530 contact the opposing interface surface, the contact area is minimized, thus reducing the size of the areas that can create ideal conditions for bacteria to grow, leading to infection and possibly to the explant of the implanted device.

As would be readily apparent to those skilled in the art, the raised concentric protrusions 530 or spacing means could be deployed on either or both of the cochlear implant components to ensure that fluid is able to flow between the interface surface 520 and its corresponding interface surface. In certain such embodiments, protrusions 530 and the protrusions of the opposing surface are configured to mate with one other. In specific embodiments, the opposing protrusions interlock with one another to maintain ISP 500 in a desired location with respect to an implanted ICS.

As noted above, protrusions 530 provide a desired spacing between the opposing interface surfaces of the ICS and the ISP. In certain embodiments of the present invention, protrusions 530 are also useful in providing a surgeon with the ability to determine when an ISP 500 is properly positioned adjacent to an implanted ICS. For example, in one embodiment the ICS has a reciprocal configuration that mates with protrusions 530 to provide the surgeon with an indication of the lateral position of ISP 500 with respect to the ICS. In other words, the reciprocal configuration mates with protrusions 530 to prevent movement of the ISP in one or more directions within a plane that is substantially parallel to the lateral plane of the ICS.

The embodiments of FIG. 5 have been discussed with reference to protrusions 530 that are integrated with interface surface 520. It would be appreciated that embodiments of the present invention may also be implemented with a third component positioned between the ICS and ISP. In such embodiments, the third component may include one or more protrusions on a surface thereof that provide a desired spacing between the third component and the ICS and/or the ISP.

Whilst the present invention is described in relation to cochlear implant components, it will be appreciated that the invention will have other applications consistent with the principles described in the specification which may be directed to a range of implantable components having interface surfaces which may be in close proximity or contact with each other.

Figure 6:
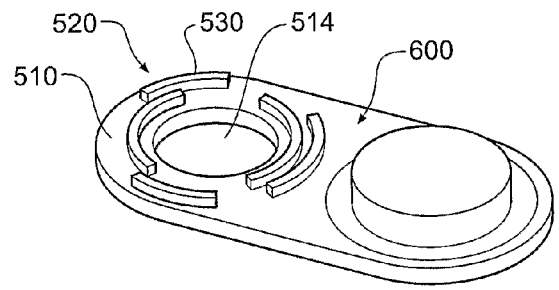
FIG. 6 is a bottom perspective view of an interface surface of an ISP unit according to a second illustrative embodiment of the present invention.

Referring now to FIG. 6, there is shown a similar arrangement to that shown in FIG. 5. However, in this embodiment the silicone in the center of the coil portion 510 of the ISP 600 is removed to form a central circular aperture 514 to further eliminate dead space that would otherwise form at interface surface 520. Because there is no second magnet, correct placement relative to the ICS would need to be achieved by mechanical means (i.e. engagement with features on the first device, such as the reciprocal arrangement described above).

Figure 7:
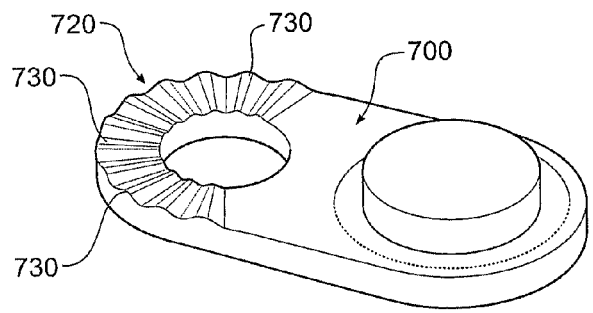
FIG. 7 is a bottom perspective view of an interface surface of an ISP unit according to a third illustrative embodiment of the present invention.

Referring now to FIG. 7, there is shown an interface surface 720 of an ISP 700 having molded radial (rather than circumferential) ridges 730 into the interface surface 720. That is, rather than protrusions which extend circumferentially about a selected portion of surface 520 as described above with reference to FIGS. 5 and 6, in these embodiments the protrusions or ridges 730 extend outward from a selected portion of surface 720. That is, ridges 830 have a length extending along the surface and have a first end positioned at a selected surface point, and a second end positioned away from the selected point. Thus, ridges 730 provide radial lines of contact with the corresponding surface of the ICS. For optimal alignment, the magnet pocket at the center could be retained, although the alternative arrangement in which the magnet is omitted is not shown here.

Figure 8:
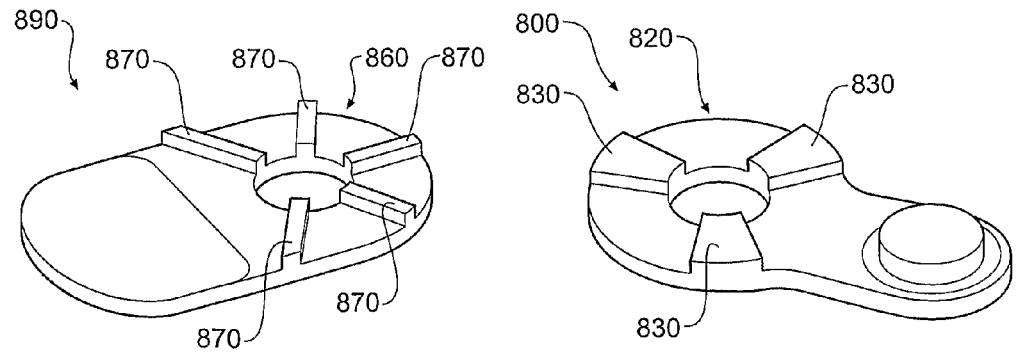
FIG. 8 incorporates a bottom perspective view of an interface surface of an ISP unit and a top perspective view of the corresponding interface surface of an ICS unit according to a fourth illustrative embodiment of the present invention.

Referring now to FIG. 8, there is shown and arrangement that is similar to FIG. 7. As shown, interface surface 820 includes ridges 830 which extend outward from a selected portion of surface 820. FIG. 8 illustrates embodiments in which fewer, more pronounced radial ridges 830 on the ISP 800 provide a greater clearance between the interface surface 820 and the corresponding interface surface 860 of the ISC 890, although the contact area and overall thickness may be increased as compared to the previous embodiments. Additionally, this embodiment shows mating radial ridges 870 deployed on the corresponding (opposing) surface 860 of the ICS 890. In this embodiment the radial ridges 830, 870 mate between each other, thereby providing a gap to allow fluid to flow between the ISP 800 and the ICS 890 and furthermore to aid in aligning these components with respect to each other. In another embodiment, the radial ridges 830, 870 are arranged to abut against each other.

In another embodiment, the spacing means used to space the interface surface of the two cochlear implant components may include a biological absorbable material forming a separation layer between the electromagnetic coil portions of the ISP and ICS that functions to hold these coil portions in place a spaced distance from each other. After time, the absorbable material will gradually dissolve allowing the fibrous tissue to replace the absorbable material in the process forming a tissue layer between the coil portions. In this manner, these interface surfaces are kept from direct physical contact with each other, thereby minimizing the risk of infection. A non-exhaustive list of suitable biological absorbable materials include bioresorbable polymers such as homopolymers of lactides and glycolide, copolymers of these monomers and copolymers based on these with e-caprolactone, tremethylene carbonate or tyrosine carbonate. Poly(hydrolxybutyrate), poly(hydroxybutyrate-co-valerate), polyorthoesters, polyesteramides and poly (propylene fumarate) based materials may also be employed.

Figure 9:
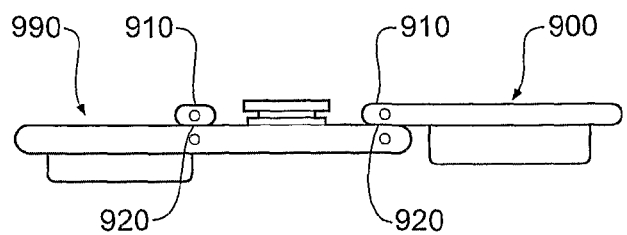
FIG. 9 is a side sectional view of a combined cochlear implant assembly according to a fifth illustrative embodiment of the present invention.
Figure 10:
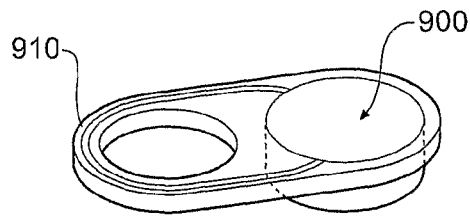
FIG. 10 is a top perspective view of the ISP unit of the combined cochlear implant assembly illustrated in FIG. 9.

Referring now to FIGS. 9 and 10, there is shown another embodiment of the present invention where the standard disc shape electromagnetic coil portion 910 is modified on the ISP 900 to a donut shape, in which case the only contact area 920 between the two cochlear implant components is limited to respective the coil "rings" on the ISP 900 and ICS 990. Thus, ISP 900 and ICS 990 have a small contact area 920 that is sufficient to provide inductive communication. In this embodiment, it is assumed that the second implant (i.e. ISP 900) does not require its own magnet and accordingly coil alignment is achieved manually with the ICS 990.

Figure 11:
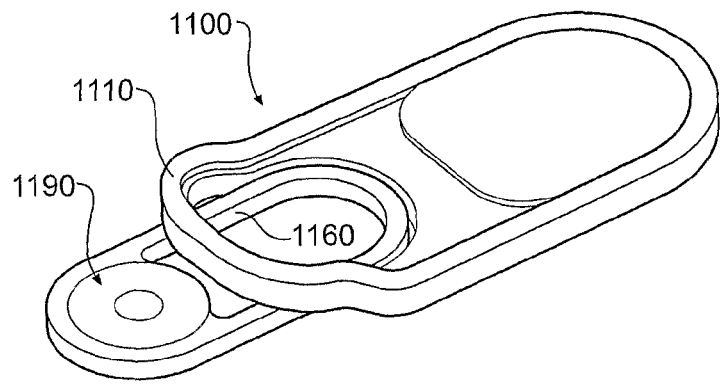
FIG. 11 is a top perspective view of a combined cochlear implant assembly according to a sixth illustrative embodiment of the present invention.
Figure 12:
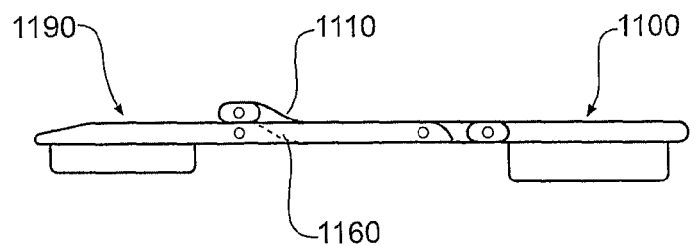
FIG. 12 is a side sectional view of the combined cochlear implant assembly illustrated in FIG. 11.

Referring now to FIGS. 11 and 12, there is shown another alternative embodiment of the present invention which involves positioning the second coil portion 1110 of the ISP 1100 around the original coil portion 1160 of the ICS unit 1190 but on a larger diameter, at least for about 330 degrees where it crosses the original coil portion 1160. In this manner, the two coil portions 1110, 1160 sit substantially in the same plane (as best seen in FIG. 12), rather than on top of each other.

A further embodiment includes providing rigid loops (made from a non-metallic material to avoid interference with the radio frequencies (RF)) extending from the outer coil 1110 of the ISP 1100 over the inner coil 1160 of the ICS 1190, through which screws could be placed to hold the two coils in the correct relationship and to also form an effective seal between the surfaces of the two coil moldings. In another embodiment, the second coil is an insulated wire laid in a holding structure on the original disc such as clips, bendable tabs, tracks or receptacles which extend from the outer circumference at discrete locations to retain the second coil firmly in place in the process ensuring that there is no body fluids retained at these join points. This would then function to minimize the area of contact between the two coils, thereby minimizing the risk of infection.

Figure 13:
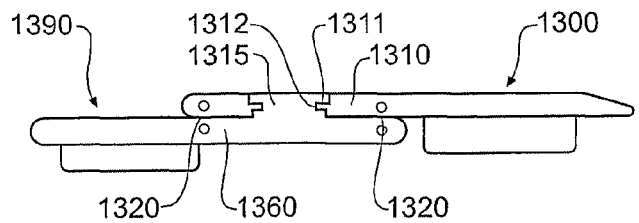
FIG. 13 is a side sectional view of a combined cochlear implant assembly according to a seventh illustrative embodiment of the present invention.
Figure 14:
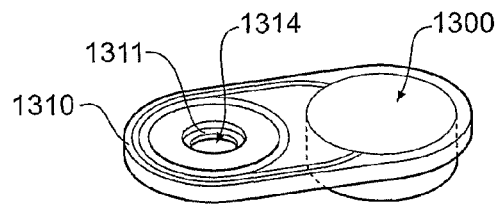
FIG. 14 is a top perspective view of the ISP unit of the combined cochlear implant assembly illustrated in FIG. 13.

Referring now to FIGS. 13 and 14, there is shown another embodiment of the present invention which includes the use of biocompatible adhesives to join and seal the coil portions 1310, 1360 of the first and second cochlear implant components 1300, 1390. Adhesives such as octyl-2 cyanoacrylate can be used intra-operatively providing excellent location and sealing. As shown in FIG. 14, the hole or aperture 1314 in the centre of the coil area of the ISP 1300 has a geometry which in this embodiment incorporates a tongue 1311 and groove 1312 arrangement to enable it to "snap" into location over the spigot 1315 of the ICS 1390, after the adhesive is applied to the interface and corresponding interface surfaces 1320.

Figure 15:
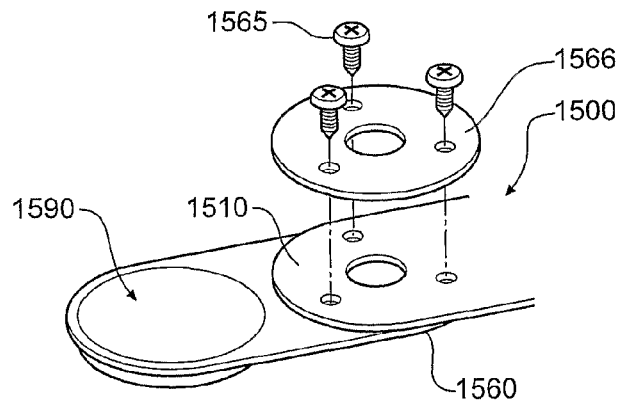
FIG. 15 is an exploded view of a combined cochlear implant assembly according to an eighth illustrative embodiment of the present invention.
Figure 16:
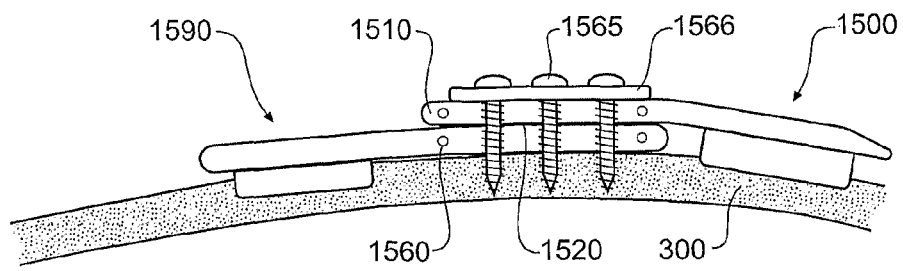
FIG. 16 is a side sectional view of the combined cochlear implant assembly illustrated in FIG. 15.

Referring now to FIGS. 15 and 16, there is shown another illustrative embodiment of the present invention which includes a rigid plate 1566 formed of biocompatible plastic such as ultra-high molecular weight polyethylene (UHMWPE) to avoid interference with the electromagnetic properties of the RF link between the communication coils, which is screwed to the skull 300 of the recipient through the coil portions 1510, 1560 of the ISP 1500 and ICS 1590 during the implant procedure such that the two parts are squeezed together as the screws 1565 are tightened.

The pressure created by screws 1565 functions to eliminate spaces between the mating surfaces 1520 in the process sealing these surfaces together. This embodiment also removes the need for a second magnet, which then preserves the current magnetic signature of the system. This can be important for effective use of diagnostic magnetic resonance imaging (MRI). The screws 1565 would provide the correct alignment between the two coils 1510, 1560.

Figure 17:
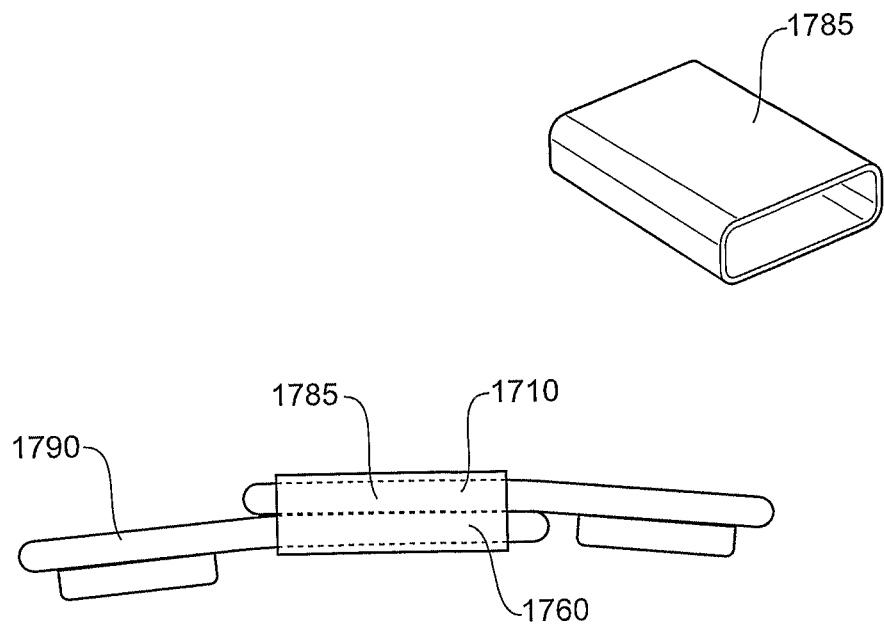
FIG. 17 is a side sectional view of a combined cochlear implant assembly according to a ninth illustrative embodiment of the present invention.

Referring now to FIG. 17, there is shown another illustrative embodiment of the present invention including a sock member 1785 made from a flexible, biocompatible material, such as silicone rubber, to surround the two coil portions 1710, 1760 of the ISP 1700 and ICS 1790 and thereby hold and seal them together.

In another illustrative embodiment, sock or sleeve member 1785 may be formed from a semi-rigid material and further incorporate a hygroscopic formed from hygroscopic material such as modified silicone. As the hygroscopic material absorbs fluid from the body after implantation, it will swell and provide a compressive force thereby causing the two coil portions 1710, 1760 to come into compression against each other, thereby sealing these two interface surfaces together. In an alternative embodiment, one or both of the coil portions 1710, 1760 may include an outwardly facing hygroscopic portion which on absorption of fluid and on interaction with the inner wall of sock or sleeve member 1785 will again provide a compressive force causing coil portions 1710, 1760 to come into compression.

Figure 18:
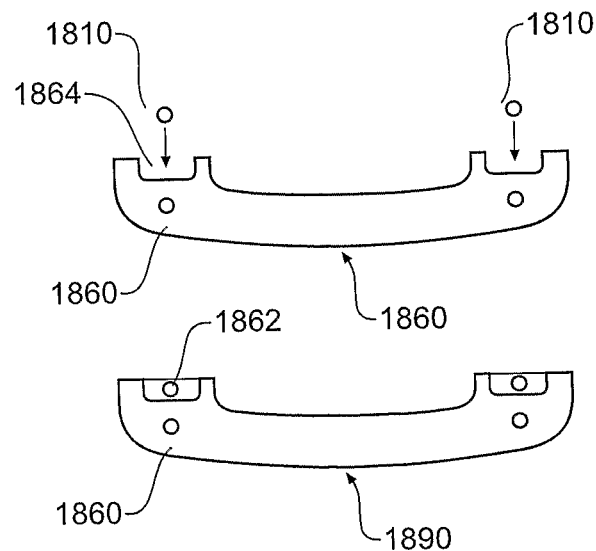
FIG. 18 incorporates exploded and assembled side sectional views of a combined cochlear implant assembly according to a tenth illustrative embodiment of the present invention.

Referring now to FIG. 18, there is shown another illustrative embodiment of the present invention where insulated wire 1810 corresponding to the coil portion 1310 of the ISP (see for example FIGS. 13 and 14) is laid down into a channel 1864 or receiving region in the disc of the ICS 1890 located above coil portion 1860. The channel 1864 is then filled with a biocompatible silicone or other filler/adhesive material 1862 intra-operatively, to secure the wire 1810 and fill the void or channel 1864.

Figure 19:
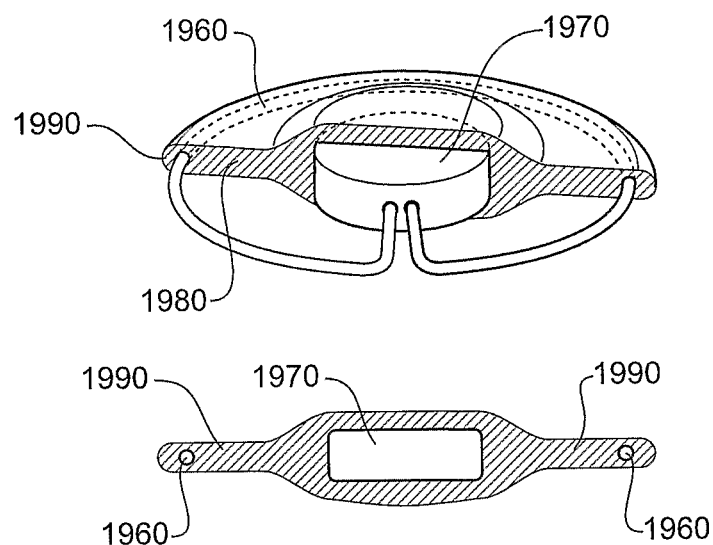
FIG. 19 incorporates cutaway front perspective and side sectional views of an ICS unit having a coil deployed about a central body portion.

Referring now to FIG. 19, there are shown front perspective and side sectional views of an ICS unit 1990 having a coil 1960 deployed about a central body portion 1970 that incorporates the cochlear stimulator circuitry that drives the electrode array as described earlier. In this embodiment, the coil 1960 is enclosed in silicone rubber 1980 or other suitable biocompatible material as is known in the art, this arrangement having a reduced footprint when compared to those cochlear implant components where the coil extends from the side of the main housing or body portion. In some situations, this can provide for the better alignment of overlapping coils.

Figure 20:
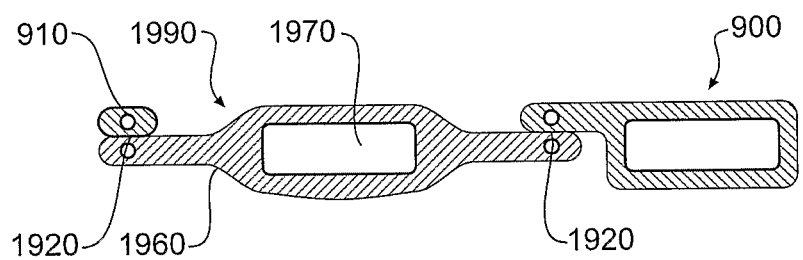
FIG. 20 is a side sectional view of the ICS unit illustrated in FIG. 19 in combination with an ISP unit to form a combined cochlear implant assembly according to an illustrative eleventh embodiment of the present invention.

Referring now to FIG. 20, there is shown a side sectional view of the ICS unit 1990 illustrated in FIG. 19 in combination with an ISP unit 900 similar to that depicted in FIG. 10 to form a combined cochlear implant assembly according to a further illustrative embodiment of the present invention. As would be appreciated by those skilled in the art, the arrangement of the implant components may be reversed with the ISP unit 900 having a central body portion enclosing the speech processing electronics (i.e. the first device) and the ICS 1990 having a coil extending to the side from a body containing the cochlear stimulator circuitry (i.e. the second device). In this embodiment, spacing means (not shown) such as depicted in any one of FIGS. 5 to 8 or equivalent are incorporated on one or more of the interface surfaces 1920 between the coil portions 910, 1960 of either first or second device or both devices, thereby allowing fluid to flow between the interface surfaces.

Figure 21:
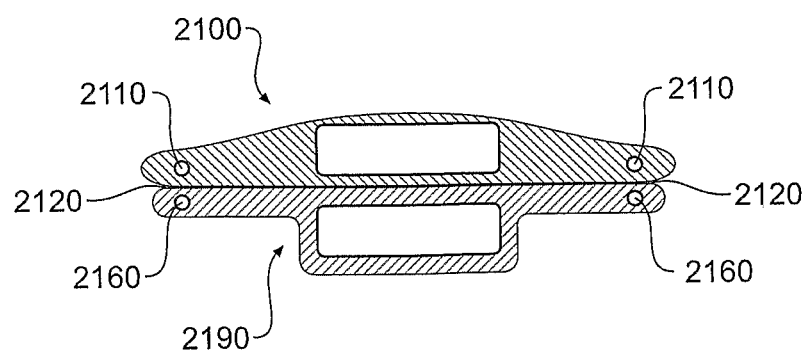
FIG. 21 is a side sectional view of the ICS unit illustrated in FIG. 20 in combination with an ISP unit also having a coil deployed about a central body portion.

Similarly, in another illustrative embodiment depicted in FIG. 21, both components 2100, 2190 are of the central body type configuration having aligned top and bottom coil portions 2110, 2160 with the interface surfaces 2120 between the first and second devices 2100, 2190 also incorporating spacing means such as has been described previously (not shown). As would be apparent to those skilled in the art, the present invention may be applied to cochlear implant components having various configurations.

To further improve the efficacy of the present invention a surface treatment may be added to mating surfaces to kill bacteria. This could be in the form of a chemical surface treatment, a drug-eluting coating, or the application of antimicrobial treatments intra-operatively.

Figure 22:
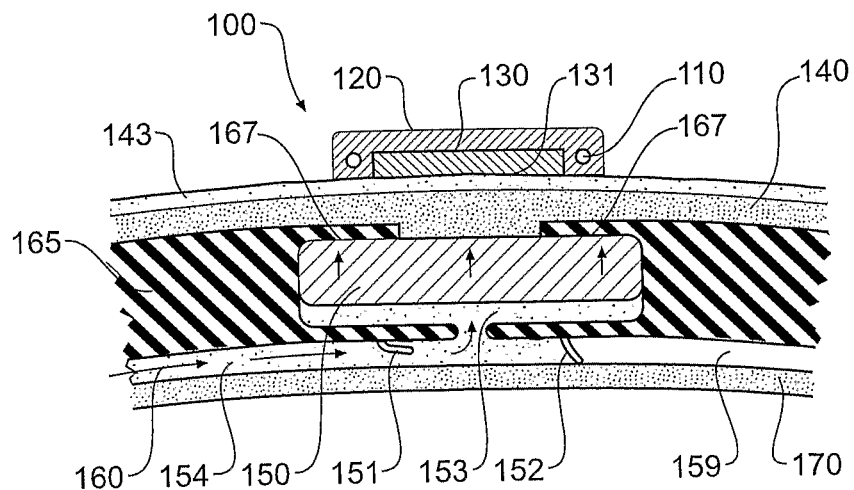
FIG. 22 is a side sectional view of a pumping assembly for pumping an in vivo fluid from a region surrounding a cochlear implant assembly depicting the in flow of body fluid according to a thirteenth illustrative embodiment of the present invention.
Figure 23:
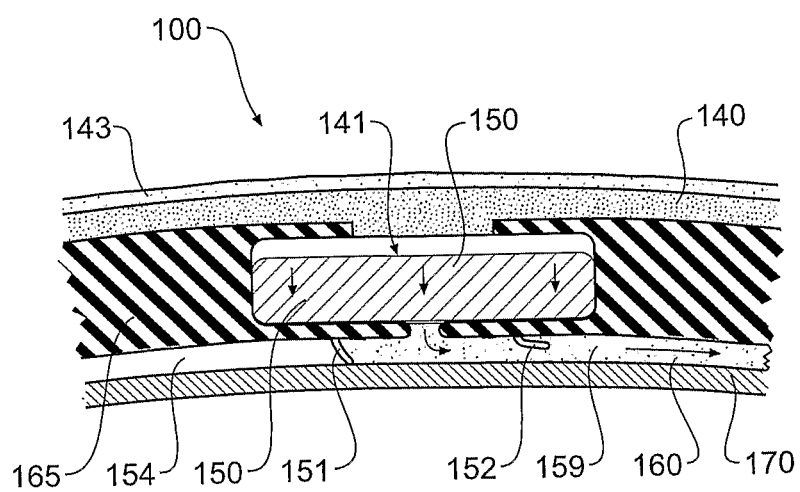
FIG. 23 is a side sectional view of the pumping assembly illustrated in FIG. 22 depicting the out flow of body fluid from the pumping surface.

Referring now to FIGS. 22 and 23, there is shown a pumping arrangement 100 for pumping a fluid 160 employing an internal magnet 150 functioning as magnetically active member residing in a surrounding cavity 141 formed in a resilient silicon layer 165. In this illustrative embodiment, magnet 150 forms part of an implanted cochlear component such as an ICS which is implanted between fibrous tissue layers 140 and 170. Pumping arrangement 100 is actuated by the magnet 130 of the external coil 110 of an external cochlear component such as a standard simulation processor (SP) 120 applied to an external region 131 of the skin 143 corresponding to the location of ICS. When the external coil 110 is positioned over internal magnet 150, such as when the SP is in use, the magnetic force provided by external coil 110 attracts the implanted magnet 150 upwards (as depicted in FIG. 22), which flexes against a roof portion 167 of silicon layer 160 in the process opening up a void or cavity 153 beneath the implanted magnet 150 and drawing in internal body fluid 160 via an input flow channel 154 that surrounds the implant past one way silicone flap valve 151.

When the external coil 110 is removed, such as when a user removes the external SP at night, the implanted magnet 150 returns to its initial position (as shown in FIG. 23), due to the restoring force provided by the silicone layer 160 surrounding the implanted magnet 150, thereby displacing the body fluid 160 that has been drawn into the void 153 via second one way flap valve 152 and out through output flow channel 159. One way flap valve 151 functions to prevent fluid 160 from flowing back along the path through which it entered. In this way, body fluid 160 may be regularly exchanged between two implant regions, thereby preventing the build up of bacteria. Additionally, the input and output flow channels 154, 159 could be routed through channels formed by the mating of the interface surfaces to specifically prevent bacterial build up in this area by the flushing mechanism as described previously.

In another illustrative embodiment, pumping arrangement 100 may be employed to pump a general in vivo fluid such as drug which may take the form of a pain killer or other therapeutic agent from a vessel located either within or outside of the body via input flow channel and out via output flow channel to a desired site within the body to provide pain relief. In this embodiment, the pumping arrangement would be implanted close to the region that requires pain relief or delivery of the therapeutic agent and then actuated by suitable application of an external magnetic force as is desired.

All documents, patents, journal articles and other materials cited in the present application are hereby incorporated by reference.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

The invention claimed is:

1. A cochlear implant system, comprising:
a first implantable component having a first interface surface; and
a second implantable component having a second interface surface comprising one or more integrated protrusions extending therefrom configured to mate with the first interface surface so as to:
provide a desired spacing between the first and second interface surfaces; and
maintain the second implantable component in a desired location with respect to the first implantable component, wherein the desired spacing allows fluid external to the implant system to freely flow between the first interface surface and the second interface surface.

2. The cochlear implant system of claim 1, wherein the one or more protrusions are positioned on said second interface surface so as to allow the passage of fluid between the first and second implantable components.

3. The cochlear implant system of claim 1, wherein at least one of the one or more one protrusions has a cross-sectional semi-circular shape.

4. The cochlear implant system of claim 1, wherein the at least one protrusion has a cross-sectional substantially circular shape.

5. The cochlear implant system of claim 1, wherein the one or more protrusions comprise a plurality of protrusions each having a length extending along the second interface surface, and each having a first end disposed at a selected point on the second interface surface, and a second end positioned away from the selected surface point.

6. The cochlear implant system of claim 1, wherein the first interface surface comprises:
at least one reciprocal configuration configured to interlock with at least one of the one or more protrusions extending from the second interface surface to prevent undesired lateral movement of the second implantable component with respect to the first implantable component.

7. The cochlear implant system of claim 1, wherein the one or more protrusions comprise a biological absorbable material.

8. The cochlear implant system of claim 1, wherein the first interface surface comprises at least one protrusion extending therefrom configured to mate with at least one of the one or more protrusions extending from the second interface surface.

9. The cochlear implant system of claim 8, wherein the distal end of the at least one protrusion extending from the first interface surface is configured to mate with the distal end of the at least one protrusion extending from the second interface surface.

10. The cochlear implant system of claim 8, wherein the at least one protrusion extending from the first interface surface is configured to mate with the at least one protrusion extending from the second interface surface to prevent lateral movement of the second implantable component with respect to the first implantable component.

11. The cochlear implant system of claim 1, further comprising:
a sleeve member formed from a biocompatible material configured to be disposed over the first and second implantable components and to force one of the first and second interface surfaces toward the other interface surface.

12. The cochlear implant system of claim 1, further comprising:
an implantable hygroscopic portion configured to absorb fluid from a recipient after implantation to provide a compressive force to force one of the first and second interface surfaces toward the other interface surface.

13. The cochlear implant system of claim 1, further comprising:
a pumping assembly configured to pump an in vivo fluid between the space provided between the first and second interfaces interface surfaces by the one or more protrusions.

14. The cochlear implant system of claim 13, wherein:
the pumping assembly includes a magnetically active member; and
on application and removal of a magnetic force to an external region of a recipient of the implantable component, the magnetically active member is caused to pump the in vivo fluid.

15. An implantable medical device, comprising:
a first implantable component having a first interface surface; and
a second implantable component having a second interface surface comprising one or more integrated protrusions extending therefrom configured to mate with the first interface surface so as to:
  provide a desired spacing between the first and second interface surfaces; and
  maintain the second implantable component in a desired location with respect to the first implantable component,
  wherein the desired spacing allows fluid external to the implantable medical device to freely flow between the first interface surface and the second interface surface.

16. The medical device of claim 15, wherein the one or more protrusions are positioned on said second interface surface so as to allow the passage of fluid between the first and second implantable components.

17. The medical device of claim 15, wherein at least one of the one or more one protrusions has a cross-sectional semicircular shape.

18. The medical device of claim 15, wherein the at least one protrusion has a cross-sectional substantially circular shape.

19. The medical device of claim 15, wherein the one or more protrusions comprise a plurality of protrusions each having a length extending along the second interface surface, and each having a first end disposed at a selected point on the second interface surface, and a second end positioned away from the selected surface point.

20. The medical device of claim 15, wherein the first interface surface comprises:
at least one reciprocal configuration configured to interlock with at least one of the one or more protrusions extending from the second interface surface to prevent undesired lateral movement of the second implantable component with respect to the first implantable component.

21. The medical device of claim 15, wherein the one or more protrusions comprise a biological absorbable material.

22. The medical device of claim 15, wherein the first interface surface comprises at least one protrusion extending therefrom configured to mate with at least one of the one or more protrusions extending from the second interface surface.

23. The medical device of claim 22, wherein the distal end of the at least one protrusion extending from the first interface surface is configured to mate with the distal end of the at least one protrusion extending from the second interface surface.

24. The medical device of claim 22, wherein the at least one protrusion extending from the first interface surface is configured to mate with the at least one protrusion extending from the second interface surface to prevent lateral movement of the second implantable component with respect to the first implantable component.

25. The medical device of claim 15, further comprising:
a sleeve member formed from a biocompatible material configured to be disposed over the first and second implantable components and to force one of the first and second interface surfaces toward the other interface surface.

26. The medical device of claim 15, further comprising:
an implantable hygroscopic portion configured to absorb fluid from a recipient after implantation to provide a compressive force to force one of the first and second interface surfaces toward the other interface surface.

27. The medical device of claim 15, further comprising:
a pumping assembly configured to pump an in vivo fluid between the space provided between the first and second interface surfaces by the one or more protrusions.

* * * * *